(12) United States Patent
Kato et al.

(10) Patent No.: US 12,011,391 B2
(45) Date of Patent: Jun. 18, 2024

(54) OCULAR IMPLANT

(71) Applicant: InnFocus, Inc., Miami, FL (US)

(72) Inventors: Yasushi Pedro Kato, Weston, FL (US); Leonard Pinchuk, Miami, FL (US)

(73) Assignee: InnFocus, Inc., Miami, FL (US)

( * ) Notice: Subject to any disclaimer, the term of this patent is extended or adjusted under 35 U.S.C. 154(b) by 344 days.

(21) Appl. No.: 17/186,803

(22) Filed: Feb. 26, 2021

(65) Prior Publication Data
US 2021/0267798 A1    Sep. 2, 2021

Related U.S. Application Data

(60) Provisional application No. 62/982,444, filed on Feb. 27, 2020.

(51) Int. Cl.
*A61F 9/007* (2006.01)
*A61F 9/00* (2006.01)

(52) U.S. Cl.
CPC ........ *A61F 9/00781* (2013.01); *A61F 9/0017* (2013.01); *A61F 2240/001* (2013.01)

(58) Field of Classification Search
CPC ................ A61F 9/00781; A61F 9/0017; A61F 2240/001; A61F 2220/0008; A61F 2230/0065; A61F 2250/0067; A61F 9/00772; A61F 2250/0068; A61F 9/007; A61F 2002/30784; A61F 2009/00891; A61F 2/14–2/147; A61F 2/15; A61F 2/16–2/1659; A61F 2002/1681–2002/169053; A61F 2/1694–2002/1699; A61M 27/00; A61M 31/002; A61M 27/002; A61M 37/00; A61M 2210/0612; A61M 2205/04; A61M 5/14276; A61K 47/34; A61K 9/0051;
(Continued)

(56) References Cited

U.S. PATENT DOCUMENTS

| 4,722,724 A | * | 2/1988 | Schocket | ............ A61F 9/00781 |
| | | | | 604/294 |
| 5,178,604 A | * | 1/1993 | Baerveldt | ............ A61M 27/002 |
| | | | | 604/9 |

(Continued)

OTHER PUBLICATIONS

Pinchuk, Wilson, Barry, Schoephoerster, Parel, Kennedy, Medical applications of poly(styrene-block-isobutylene-block-styrene)("SIBS"), Nov. 5, 2007, ScienceDirect, pp. 449-454 (Year: 2007).*

*Primary Examiner* — Nicholas J. Weiss
*Assistant Examiner* — Brandon W. Levy
(74) *Attorney, Agent, or Firm* — Gordon & Jacobson, P.C.

(57) ABSTRACT

A device implantable into the eye that includes an elongate duct portion defining two lumens that extend parallel to one another from a distal end to a neck spaced longitudinally from the distal end, a second portion including two tubular segments that extend or flare outwardly from the neck opposite one another with at least one additional tubular segment that extends between the two tubular segments such that the tubular segments of the second portion form a tubular loop that surrounds an interior area. The tubular segments of the second portion that form the tubular loop define a common lumen with a plurality of outlets that are in fluid communication with the two lumens of the duct portion to permit fluid to flow through the device.

12 Claims, 10 Drawing Sheets

(58) Field of Classification Search
CPC ... A61K 9/0048; A61L 2430/16; A61P 27/02; A61B 17/56; G02C 7/04
See application file for complete search history.

(56) References Cited

U.S. PATENT DOCUMENTS

| | | | |
|---|---|---|---|
| 5,338,291 A * | 8/1994 | Speckman | A61F 9/00781 604/9 |
| 5,741,331 A | 4/1998 | Pinchuk | |
| 6,102,939 A | 8/2000 | Pinchuk | |
| 6,197,240 B1 | 3/2001 | Pinchuk | |
| 6,545,097 B2 | 4/2003 | Pinchuk et al. | |
| 7,431,709 B2 | 10/2008 | Pinchuk et al. | |
| 7,594,899 B2 | 9/2009 | Pinchuk et al. | |
| 7,837,644 B2 | 11/2010 | Pinchuk et al. | |
| 9,101,444 B2 | 8/2015 | Pinchuk | |
| 2004/0106906 A1 * | 6/2004 | Yaacobi | A61F 9/0017 604/294 |
| 2004/0210181 A1 * | 10/2004 | Vass | A61F 9/00781 604/8 |
| 2005/0261624 A1 * | 11/2005 | Wilcox | A61F 9/00781 604/27 |
| 2007/0088432 A1 * | 4/2007 | Solovay | A61F 9/00781 623/4.1 |
| 2011/0184358 A1 * | 7/2011 | Weiner | A61F 9/0026 424/428 |
| 2015/0148729 A1 * | 5/2015 | Pinchuk | A61M 27/002 604/8 |
| 2016/0109726 A1 * | 4/2016 | Tai | G02C 7/041 351/159.04 |
| 2019/0247227 A1 * | 8/2019 | Peyman | A61K 38/164 |

* cited by examiner

OCULAR IMPLANT

CROSS-REFERENCE TO RELATED APPLICATION(S)

The present disclosure claims priority from U.S. Provisional Pat. Appl. No. 62/982,444, filed on Feb. 27, 2020, entitled "Ocular Implant", herein incorporated by reference in its entirety.

BACKGROUND

1. Field

The present disclosure relates to medical devices for creating fluid delivery pathways in the eye, and more particularly, to medical devices for creating drainage pathway to divert aqueous humor from the anterior chamber of the eye for treatment of glaucoma.

2. State of the Art

Figure 1:
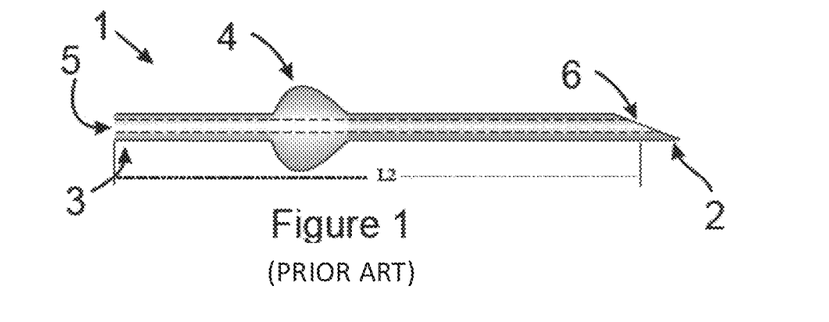
FIG. 1 is a cross-sectional schematic diagram of a prior art GDI.

InnFocus, Inc. of Miami, Florida has issued patents on glaucoma drainage devices or implants (GDIs) (e.g., U.S. Pat. Nos. 7,431,709, 7,594,899, 7,837,644 and 9,101,444), which are herein incorporated by reference in their entireties. The term "distal" in this document denotes the part of the device furthest from the surgeon implanting the device. The term "proximal" denotes the part of the device closest to the surgeon implanting the device. A typical GDI is shown in FIG. 1 and includes an elongated tubular body or tube 1 with a distal end 2 and a proximal end 3. One or more projections or fins 4 extend radially from the exterior surface of the tube 1 at an intermediate position between the distal end 2 and proximal end 3. When the GDI is implanted into the eye, the fin(s) 4 can aid in preventing migration of the tube 1 into the eye and also act as a "cork" to prevent peri-tubular leakage outside the tube. The tube 1 also includes a bevel 6 on the distal end 2. The tube 1 has an internal lumen 5 that extends from the distal end 2 to the proximal end 3. The length of the lumen 5 is labeled L2 in FIG. 1. When the GDI is implanted into the eye, the lumen 5 provides a flow path for drainage of fluid from the interior of the eye (e.g., drainage of aqueous humor from the anterior chamber).

Figure 2:
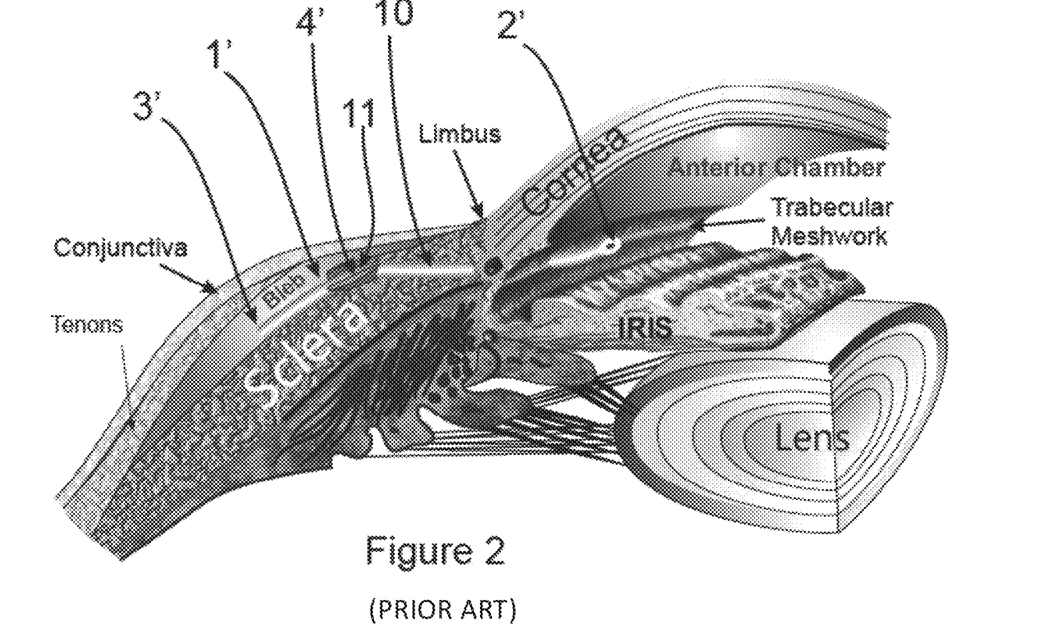
FIG. 2 is a diagram that shows an example implantation or placement of the GDI of FIG. 1 into the eye.

FIG. 2 illustrates an example implantation or placement of the GDI into the eye. In this case, the distal end or tip 2' is in the anterior chamber of the eye and the tube 1' extends under the limbus and through the sclera 10. The proximal end 3' rests in a dissected plane between the conjunctiva/Tenon's capsule and the sclera. Fluid (e.g., aqueous humor) from the anterior chamber flows through the lumen 5 of the GDI and drains into the sub-conjunctiva/Tenons space to form a small blister called a bleb. The projection or fin(s) 4' can be located posterior to the limbus and can be buried in a small pocket 11 cut into the sclera with a scalpel or triangular knife. The GDI is typically placed into this position by forming a needle tract (or tissue passageway) through the scleral pocket 11 under the limbus (area 10) and into the anterior chamber. The tube 1' of the GDI can be grasped by forceps or other means and inserted into this needle tract.

The GDI (particularly the tube 1 and possibly the fin(s) 4 of the GDI) is typically made from a soft and flexible material such as poly(styrene-block-isobutylene-block-styrene) (SIBS) of Shore hardness less than 60 A. In embodiments, the GDI can be made from SIBS of Shore hardness in the range 30 A to 50 A, more preferably in the range 35 A to 45 A, and possibly with a Shore hardness of 40 A. In embodiments, the diameter of the lumen 5 of the tube 1 can range from 0.04 mm to 0.1 mm, more preferably in the range 60 μm to 80 μm and can be 70 μm. The outer diameter of the tube 1 can range from 0.2 mm to 0.8 mm and can be 0.35 mm in embodiments. In these embodiments, the soft material and size and the tube 1 on both sides of the fin(s) 4 renders the tube 1 floppy and thus difficult to push through the needle tract under the limbus and into the anterior chamber.

Implanting the device is traditionally accomplished with forceps which are used to hold the GDI near its distal tip 2' and incrementally move the GDI through the pocket and needle tract and into the anterior chamber. The proximal end 3 of the GDI is eventually located in a bleb between the Tenon's capsule and the sclera. Aqueous humor conducted by the GDI drains into the bleb. The GDI relies on the surrounding bleb remaining open and not scarring over the tube, which could block the outlet of the tube. Blocking the outlet of the tube would prevent drainage of aqueous humor and result in elevated pressure in the eye. Therefore, there is a need to avoid blockage of the outlet of the GDI.

SUMMARY

According to one aspect of the present disclosure, an ocular implant (i.e., a device implantable into the eye) is provided that includes an elongate duct portion having a longitudinal axis. The duct portion defines at least one lumen that extends from a distal end to a neck spaced longitudinally from the distal end. The ocular implant further includes a second portion that includes two tubular segments that extend or flare outwardly from the neck opposite one another relative to the longitudinal axis. The second portion includes at least one outlet in fluid communication the at least one lumen of the duct portion to permit fluid to flow through the ocular implant. In embodiments, the first duct portion and the second portion are formed together as a unitary structure.

In embodiments, the duct portion can include two tubes that are joined or fused together along their lengthwise extent. The two tubes define two respective lumens that extend from respective first inlets at the distal end to the neck.

In one embodiment, the two tubular segments of the second portion can extend or flare outwardly from the neck opposite one another relative to the longitudinal axis in a Y configuration.

In another embodiment, the second portion can further include at least one additional tubular segment that extends between the two tubular segments such that the tubular segments of the second portion form a loop that surrounds an interior area. The tubular segments of the second loop portion can define a common lumen extending through the loop that terminates at the neck where two ends of the common lumen are fluid connected to the two respective lumens of the two tubes of the first duct portion.

In embodiments the tubular segments of the second portion can have one or more openings or passageways that extend between the lumen of the second portion and the open interior area. Because the lumen of the second portion is in fluid communication with the two respective lumens of the first duct portion, the one or more openings provide for fluid communication between the two lumens of the first duct portion and the open interior area. It is contemplated that the ocular implant may be packaged with a suitable inserter as a glaucoma system or kit.

In embodiments, the ocular implant can be used as a GDI. In this application, the inlet(s) of the duct portion can be implanted or otherwise disposed in the anterior chamber of the eye and the second portion is implanted or otherwise disposed in a bleb or drainage cavity defined by ocular tissue, such as between Tenon's capsule and the sclera of the eye. In this configuration, aqueous fluid from the anterior chamber can be delivered through the lumen(s) of the first duct portion to the second portion and then discharged through the one or more openings of the second portion into the bleb.

In embodiments, the one or more openings of the second portion face or otherwise extend into an area that lies within the bleb. Thus, when the ocular implant is implanted in the eye and configured for use as a GDI, aqueous humor can drain through into the area within the bleb. The one or more openings are preferably located between opposed surfaces of the second looped portion, where such opposed surfaces are configured to contact and preferably seal to tissue surfaces that define the bleb (e.g., a bleb defined between Tenon's capsule and the sclera of the eye). Thus, fluid discharged through the one or more openings can flow into the bleb.

In embodiments, the first duct portion and second portion of the ocular implant can be formed together as a unitary structure. In embodiments, the first duct portion and the second portion can be made of SIBS.

In accordance with yet another aspect of the disclosure, the ocular implant as described herein can be incorporated into a drug delivery device or system (DDS), which includes a fluid reservoir having a fluid tight wall defining a cavity that is configured to contain a liquid drug. In embodiments, at least a portion of the wall of the fluid reservoir is self-sealing and is configured to be punctured by a syringe needle for filling the fluid reservoir with liquid (e.g., a drug). The cavity also contains a part portion (e.g., the looped portion or Y portion) of the ocular implant described herein. The duct portion of the ocular implant extends from the second portion and through the wall of the reservoir with a fluid tight seal between an outer surface of the duct portion and the wall of the reservoir. The DDS can be used by implanting the reservoir in a space in the eye, and disposing the outlet(s) of the at least one lumen of the duct portion at a desired drug delivery location in the eye. One or more openings or inlets can be provided by the second portion of the ocular implant disposed in the reservoir and such inlet(s) can be fluidly coupled by the lumens of the ocular implant to the outlet(s) of the duct portion. Thus, the liquid drug in the reservoir can enter the inlet(s), flow through the lumens of the ocular implant to the outlet(s) of the duct portion at the drug delivery site. Thus, when used as part of a drug delivery device or system, the flow through the ocular implant is from that portion of the ocular implant disposed in the reservoir and through the duct portion of the ocular implant, which is the reverse flow direction through the ocular implant described above when used as a GDI.

According to another aspect of the disclosure, a method of making an ocular implant as described herein includes receiving an elongate tube having a body that extends from a first open end to a second open end opposite the first open end. The body defines a lumen extending through the body between the first and second open ends. The body has a first portion extending from the first open end, a second portion extending from the second open end, and an intermediate portion extending from the first portion to the second portion. The body has a continuous external surface. The method of making the ocular implant also includes joining the outer wall of the body along the first portion and to the outer wall of the body along the second portion, which forms the intermediate portion into a loop that surrounds an open interior area. The body of the intermediate portion (loop) defines a lumen extending therethrough, and the ends of this lumen are fluidly coupled to the two lumens of the joined first and second body portions.

In embodiments, one or more openings or passageways can be defined through the wall of the body of the intermediate portion (loop). In this manner, the one or more openings or passageways extend between the lumen of the intermediate body portion and the open interior area.

In embodiments, the first portion of the body has a first length, the second portion of the body has a second length that matches the first length, and the first and second portions are joined together along their entire lengths. Furthermore, the first open end of the first portion of the body can be aligned flush with the second open end of the second portion of the body.

Also, in embodiments, the intermediate portion can define two or more openings through the wall of the body, and the ocular implant may be configured to temporarily close flow to at least one of the openings. For example, in an embodiment where the intermediate portion defines two openings, one of the openings can be temporarily sealed closed with sutures, semi-permanent materials, etc. and later opened in situ. As an alternative, the open ends of the first or second portions of the body can be temporarily sealed closed.

DETAILED DESCRIPTION OF THE PREFERRED EMBODIMENTS

Figure 3A:
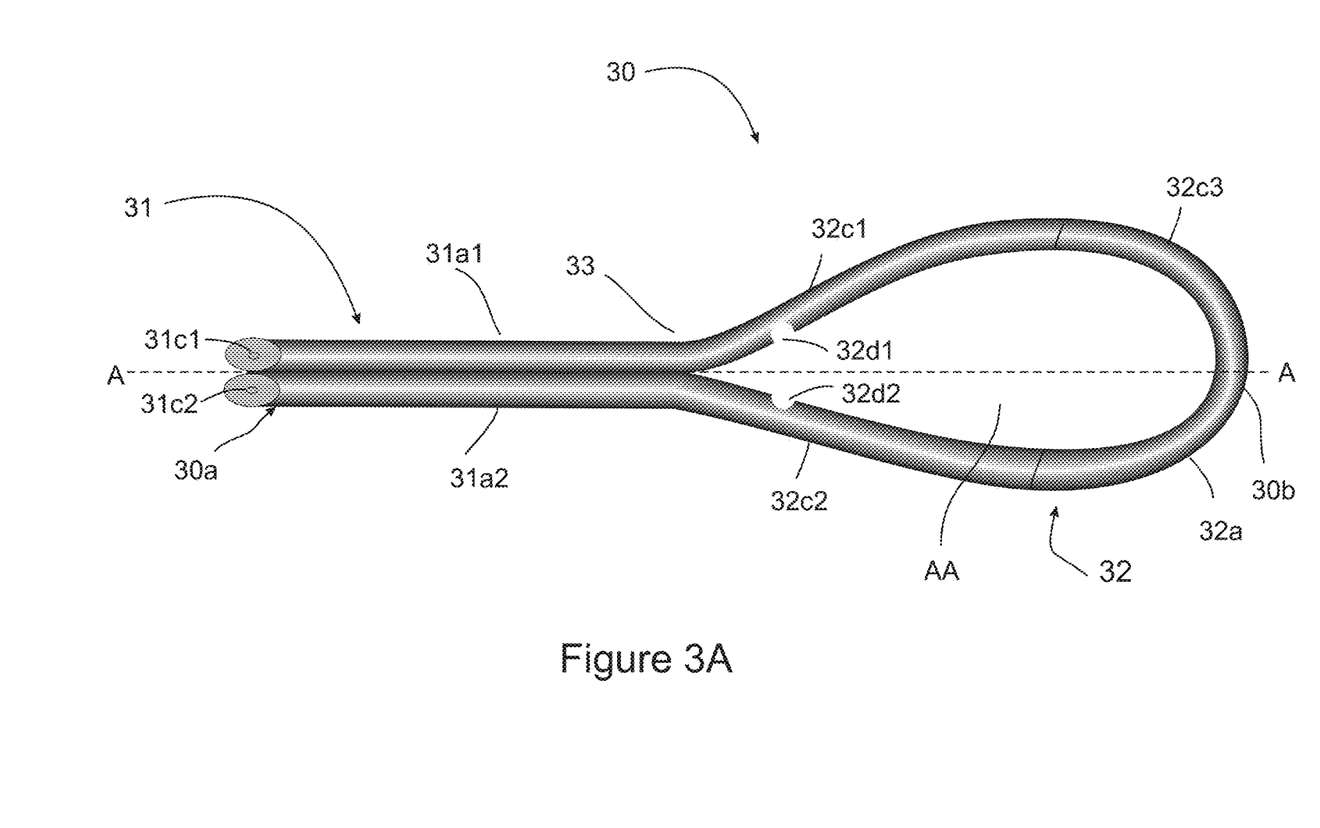
FIG. 3A shows an example embodiment of an ocular implant in accordance with the present disclosure.
Figure 3B:
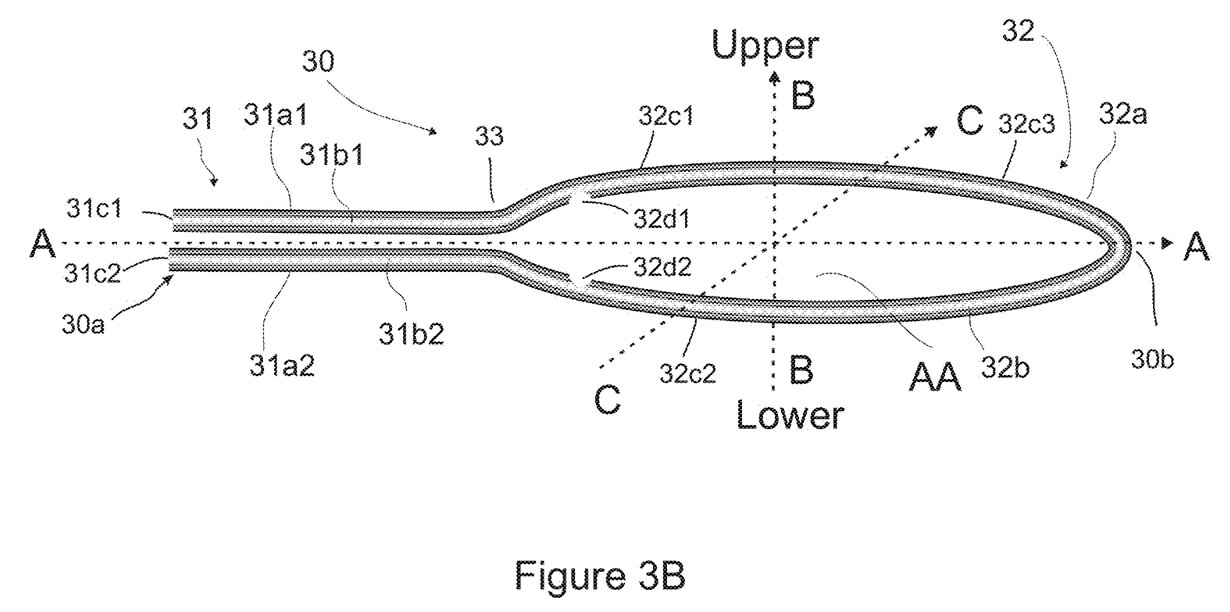
FIG. 3B is a schematic view of the flow channels of the ocular implant of FIG. 3A.

FIGS. 3A and 3B show an embodiment of an ocular implant 30, which can be used as a glaucoma drainage implant (GDI). The ocular implant 30 comprises a unitary device that can be implanted into the eye. When used as a GDI, the ocular implant 30 can drain aqueous humor from the eye to help control elevated intraocular pressure (IOP) that can contribute to glaucoma of the eye. The ocular implant 30 includes an elongated first duct portion 31 and a second loop portion 32. The ocular implant 30 resembles a tennis racquet, with the first duct portion 31 resembling the handle and shaft of the racquet and the second loop portion 32 resembling the head of the racquet. As with a racquet, the ocular implant 30 transitions from the second looped portion 32 to the first duct portion 31 at a neck or throat 33. The first duct portion 31 extends longitudinally along an axis A-A as shown. The ocular implant 30 extends along this longitudinal axis A-A from a distal end 30a to a proximal end 30b. The first duct portion 31 includes two tubes 31a1, 31a2 that are joined or fused together along their lengthwise extent. The two tubes 31a1, 31a2 define two respective internal lumens 31b1, 31b2 (FIG. 3B) that extend from respective open first ends or inlets 31c1, 31c2 at the distal end 30a of the ocular implant 30 to the neck 33. The second loop portion 32 includes a tube 32a having two tubular segments 32c1, 32c2 that extend or flare outwardly from the neck 33 opposite one another relative to the longitudinal axis A-A in a Y configuration as shown. The tube 32a of the second loop portion 32 further includes one or more additional tubular segments (one shown as 32c3) disposed between the two tubular segments 32c1, 32c2 to form a loop that surrounds an open interior area AA. The tubular segments 32c1, 32c2, 32c3 of the second loop portion 32 define a common lumen 32b (FIG. 3B) extending through the loop that terminates at the neck 33 where the two ends of the common lumen 32b are fluidly connected to the two respective lumens 31b1, 31b2 of the two tubes 31a1, 31a2 of the first duct portion 31. Furthermore, the tube 32a (e.g., tubular segments 32c1, 32c2, 32c3) can define one or more openings (e.g., two shown as 32d1, 32d2) in fluid communication with the lumen 32b of tube 32a as well as in fluid communication with the lumens 31b1, 31b2 of the tubes 31a1, 31a2 (FIG. 3B). While two openings 32d1, 32d2 are shown in FIG. 3A, one opening or more than two openings may be present in other embodiments. In the embodiment shown in FIG. 3A, the openings 32d1, 32d2 face the interior area AA.

In the embodiment shown in FIGS. 3A and 3B, the first duct portion 31 and the second loop portion 32 can be formed into a unitary structure by providing a continuous tube having a single continuous lumen therethrough and looping the single continuous tube back on itself. In this configuration, lengthwise end portions of the single tube are fused or joined to one another to form the first duct portion 31. The intermediate portion of the single tube that is disposed between the two lengthwise end portions form the second loop portion 32. The lengthwise end portions of the single tube can be fused or joined to one another by adhesive bonding, melt bonding, mechanical couplers, or other suitable means. Additionally or alternatively, the first duct portion 31 and the second loop portion 32 of the ocular implant may be discrete elements that may be coupled together at the neck 33 with suitable fluid couplings and the like.

When the ocular implant 30 is used as a GDI, the inlets 31c1, 31c2 of the first duct portion 31 can be configured for implantation in the anterior chamber of the eye and the tube 32a of the second loop portion 32 can be configured for implantation in a bleb or drainage cavity formed by ocular tissue, such as a bleb in space between Tenon's capsule and the sclera. In this configuration, ocular fluid (e.g., aqueous humor from the anterior chamber) can be transported through the ocular implant 30 from the first duct portion 31 to the second loop portion 32, which is configured to discharge the fluid through one or more openings (e.g., openings 32d1, 32d2) of the second loop portion 32 into the bleb. The one or more openings (e.g., openings 32d1, 32d2) can face the interior area AA that lies within the bleb and thus direct fluid (aqueous humor) to discharge from the second loop portion 32 into the bleb. It is also contemplated that the ocular implant may be packaged with a suitable inserter as a glaucoma system or kit.

In the embodiment shown in FIGS. 3A and 3B, the one or more openings (e.g., openings 32d1, 32d2) of the second loop portion 32 are in fluid communication with the lumen 32b of the tube 32a of the second loop portion 32 as well as in fluid communication with both lumens 31b1, 31b2 of the tubes 31a1, 31a2 of the first duct portion 31. Thus, even if one of the openings (e.g., opening 32d1) is closed or is blocked (such as from scar tissue overgrowth), fluid can still flow through the lumen 32b for discharge out one other opening (e.g., opening 32d2) as long as the one other opening is not blocked. Thus, the second loop portion 32 with the plurality of openings can provide a redundant drainage flow path for the ocular implant 30, which can mitigate pressure increase in the eye that may be caused as a result of a blockage of one of the openings.

In FIG. 3A, the ocular implant 30 is shown in a neutral, undeformed state where the second loop portion 32 has a length measured along the longitudinal axis A-A that is equal to or greater than a length of the first duct portion 31 measured along the longitudinal axis A-A. Also, as shown in FIG. 3A, the one or more openings (e.g., openings 32d1, 32d2) of the second loop portion 32 can be defined by a respective semicircular notch or cutout in the wall of the tube 32a of the second loop portion 32. The one or more openings (e.g., openings 32d1, 32d2) can be disposed on the radially inward side of the looped tube 32a (with respect to the interior lumen 32b) and face the interior area AA. In embodiments, the openings 32d can extend diametrically through the wall of the looped tube 32a from an upper surface to a lower surface of the looped tube 32a.

Figure 3C:
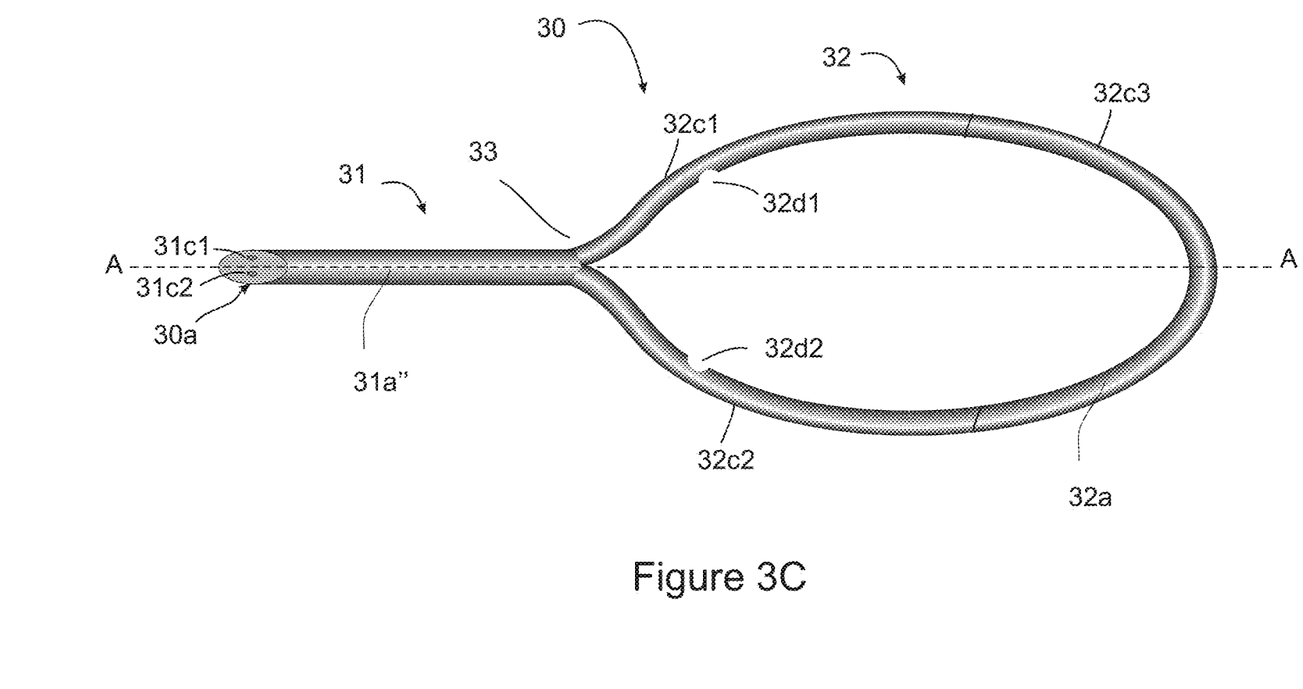
FIG. 3C shows another example embodiment of an ocular implant in accordance with the present disclosure.

While the first duct portion 31 is shown with two tubes 31a1, 31a2 and two lumens 31b1, 31b2 and two inlets 31c1, 31c2, in other embodiments the first duct portion 31 may define one or more than two inlets and lumens in fluid communication with the common lumen 32b of the looped tube 32a of the second loop portion 32. For example, in the embodiment of FIG. 3C, the first duct portion 31 includes a single tube 31a" that defines two separate internal lumens that are in fluid communication with the respective ends of the lumen 32b of the second loop portion 32 at the neck 33. Also, in other embodiments, the first duct portion 31 may include a single tube that defines one internal lumen in fluid communication with the respective ends of the lumen 32b of the second loop portion 32 at the neck 33.

Figure 4:
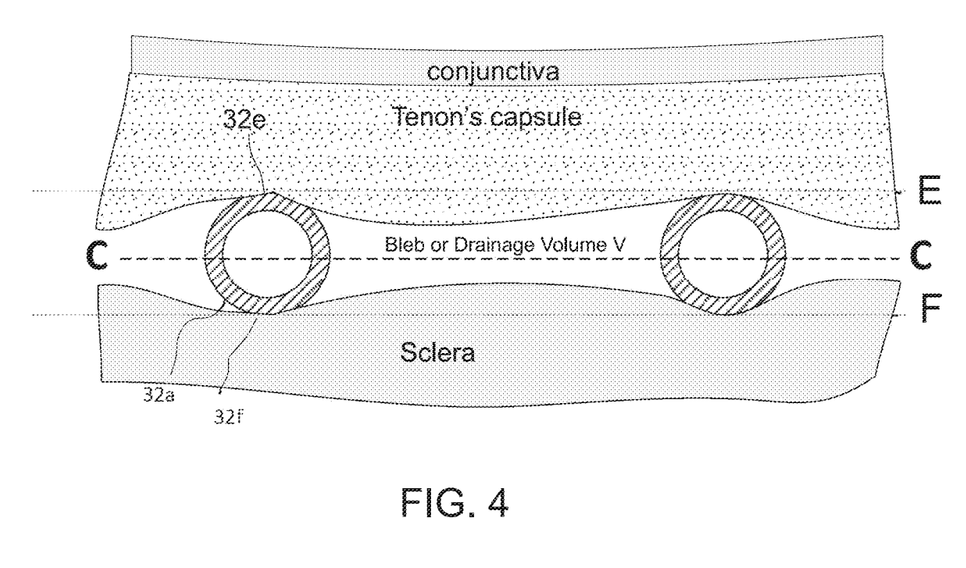
FIG. 4 is a sectional view of the ocular implant of FIG. 3A, 3B or 3C implanted into the eye.

The ocular implant 30 can be used as a GDI for implantation in a human eye. The inlets 31c1, 31c2 of the first duct portion 31 can be disposed in the anterior chamber of the eye similar to the embodiment shown in FIG. 2. Note that the tubular segments 32c1, 32c2 of the tube 32a of the second looped portion 32 extend or flare outwardly opposite one another (relative to the axis A-A) at the neck 33 in a Y configuration so that the neck 33 wedges itself into the tissue in a fluid tight manner to prevent leakage around the neck 33 and to resist further migration of the ocular implant 30 towards the anterior chamber. As shown in the cross-sectional view of FIG. 4, the second loop portion 32 can be located in a bleb (or drainage volume, labeled V) interposed between Tenon's capsule and the sclera. In this configuration, the tube 32a (e.g., tubular segments 32c1, 32c2, 32c3) of the second loop portion 32 has an upper surface 32e above axis C-C and a lower surface 32f below axis C-C. Plane E extends at points of tangency of the upper surface 32e, and a plane F extends at points of tangency of the lower surface 32f. The planes E and F are offset from one another at a distance equal to the thickness of the tube 32a. The upper surface 32e and the lower surface 32f are configured to support ocular tissue. Specifically, when implanted, the tissue of Tenon's capsule can contact and interface to the upper surface 32e and the tissue of the sclera can contact and interface to the lower surface 32f so as to enclose (preferably with sealing interfaces) the bleb or drainage volume V disposed between the opposed tissue surfaces (e.g., Tenon's capsule and sclera). When the looped tube 32a is so implanted, the surface tension of Tenon's capsule and the sclera may cause the surfaces of Tenon's capsule and the sclera to bow or curve inwardly toward axis C-C as shown. However, the diameter of the looped tube 32a can be dimensioned to prevent the tissue of the Tenon's capsule and the sclera from coming into contact with one another and possibly reducing the intended volume of the bleb. When implanted as shown in FIG. 4, the one or more openings (e.g., openings 32d1, 32d2) of the second loop portion 32 are in fluid communication with the bleb. The ocular implant 30 permits aqueous humor in the anterior chamber to flow into the inlets 31c1, 31c2 of the first duct portion 31, through the two lumens 31b1, 31b2 of the two tubes 31a1, 31a2, through separate parts of the lumen 32b provided by the tubular segments 31c1, 31c2 that are in fluid communication with the two lumens 31b1, 31b2, and then out at least one opening (e.g., of openings 32d1, 32d2) and into the bleb, where the fluid can be further transported (e.g., absorbed) through the tissues surrounding the bleb. When the ocular implant 30 is implanted as described above with respect to FIG. 4, the ocular implant 30 can be titratable by temporarily blocking one of the two lumens 31b, such as with a suture, plug, or other method.

The ocular implant 30 can be formed from a flexible elastomeric material. For example, the ocular implant 30 can be formed from SIBS, which is a biocompatible, soft, atraumatic, bioinert polymer and has proven history in the eye greater than 10-years in duration. SIBS is a polyolefinic triblock copolymer material having a triblock polymer backbone comprising poly(styrene-block-isobutylene-block-styrene). High molecular weight polyisobutylene (PIB) is a soft elastomeric material with a Shore hardness of approximately 10 A to 30 A. When copolymerized with polystyrene, it can be made at hardnesses ranging up to the hardness of polystyrene, which has a Shore hardness of 100D. Thus, depending on the relative amounts of styrene and isobutylene, the SIBS copolymer can have a range of hardnesses from as soft as Shore 10 A to as hard as Shore 100D. In this manner, the SIBS copolymer can be adapted to have the desired elastomeric and hardness qualities. Details of the SIBS copolymer are set forth in U.S. Pat. Nos. 5,741,331; 6,102,939; 6,197,240; 6,545,097, which are hereby incorporated by reference in their entirety. Although SIBS is used as a preferred example, the materials used for making the ocular implant 30 can include silicone rubber or other suitable polymeric material. In embodiments, the hardness of the elastomeric polymer material of the implant 30 can range from Shore 30 A to Shore 65D, preferably shore 40 A to 50 A. In the event that the duct portion 31 and loop portion 32 are formed from different polymeric materials (such as different SIBS materials), the duct portion 31 can be formed from an elastomeric polymer material (e.g., first SIBS material) with a hardness in the range of Shore 40 A to Shore 50 A, while the loop portion 32 can be from a different elastomeric polymer material (e.g., second SIBS material) with a hardness in the range of Shore 80 A to shore 65D and more preferably in the range of Shore 50D to Shore 55D. These material properties can provide some rigidity to the loop structure 32 to ensure that the loop does not fold on itself in the bleb.

In embodiments, when the ocular implant 30 is implanted in the eye, the duct portion 31 can extend in a straight linear path, curved linear path, segmented path or other complex curvilinear path depending on the design and material properties (e.g., hardness) of the duct portion 31. For flexible configurations of the duct portion 31, the path of the duct portion 31 can depend on placement of the duct portion 31 and the surrounding ocular tissue in the eye. Similarly, when the ocular implant 30 is implanted in the eye, the loop structure 32 can extend in a curved linear path, segmented path or other complex curvilinear path depending on the design and material properties (e.g., hardness) of the loop structure 32. For flexible configurations of the loop structure 32, the path of the loop structure 32 can depend on placement of the loop structure 32 and the surrounding ocular tissue in the eye.

In embodiments, the diameters of the lumens 31b1, 31b2 and lumen 32b can range from 0.04 mm to 0.1 mm, more preferably in the range 60 μm to 80 μm and can be 70 μm. The outer diameters of the tubular structures of first duction portion 31 and the second loop portion 32 can range from 0.2 mm to 0.8 mm and can be 0.35 mm in embodiments. In these embodiments, the soft material and size of these tubular structures can render the ocular implant 30 very flexible and floppy.

The ocular implant 30 may be formed in various ways. One example embodiment of a workflow for making the ocular implant is described hereinbelow. An elongate flexible tube is provided that has a body that extends from a first open end to a second open end opposite the first open end. The body defines a central lumen extending through the body between the first and second open ends. The body has a first portion extending from the first open end, a second portion extending from the second open end, and an intermediate portion extending between the first portion to the second portion. The body has a continuous outer surface from the first end to the second end. The intermediate portion defines at least one opening (and preferably a plurality of openings) through the side of the body where such opening(s) is (are) in fluid communication with the lumen. The elongate tube is formed into the ocular implant by fusing or joining together portions of the outer surfaces of the first and second portions of the body, which forms the intermediate portion into a loop. The first and second portions can be joined such that the loop formed by the intermediate portion surrounds an area. Also, it is preferable that equal lengths of the first and second portion are joined together and that the first and second ends of the tube are aligned flush with one another.

In accordance with another aspect of the disclosure, the structure of the ocular implant 30 described above can be incorporated into a drug delivery device or system (DDS) for delivering drugs to one or more locations in the eye, such as the anterior chamber and the posterior chamber. In order to treat certain ocular diseases, there is a need to provide a constant infusion of a liquid-form therapeutic agent (e.g., drug) within the eye. Specifically, in the treatment of wet macular degeneration, the patient undergoes monthly injections of the liquid form agent Bevacizumab (which is sold under the trade name "Avastin®"), which is an anti-VEGF drug to stop the overgrowth of the macula with blood vessels. This monthly injection is painful to the patient and bothersome to the medical providers who inject the drug. In addition, there is a risk of infection every time a needle is inserted into the eye. However, when used in a drug delivery system, the direction of flow through the ocular implant 30 that is described hereinabove for a GDI is functionally reversed for a DDS so that fluid flows from the openings 32$c$ of the tube of the second loop portion to the openings 31$c$ of the tubes of the first duct portion, where the fluid (i.e., the drugs) is discharged for therapeutic delivery.

Figure 5:
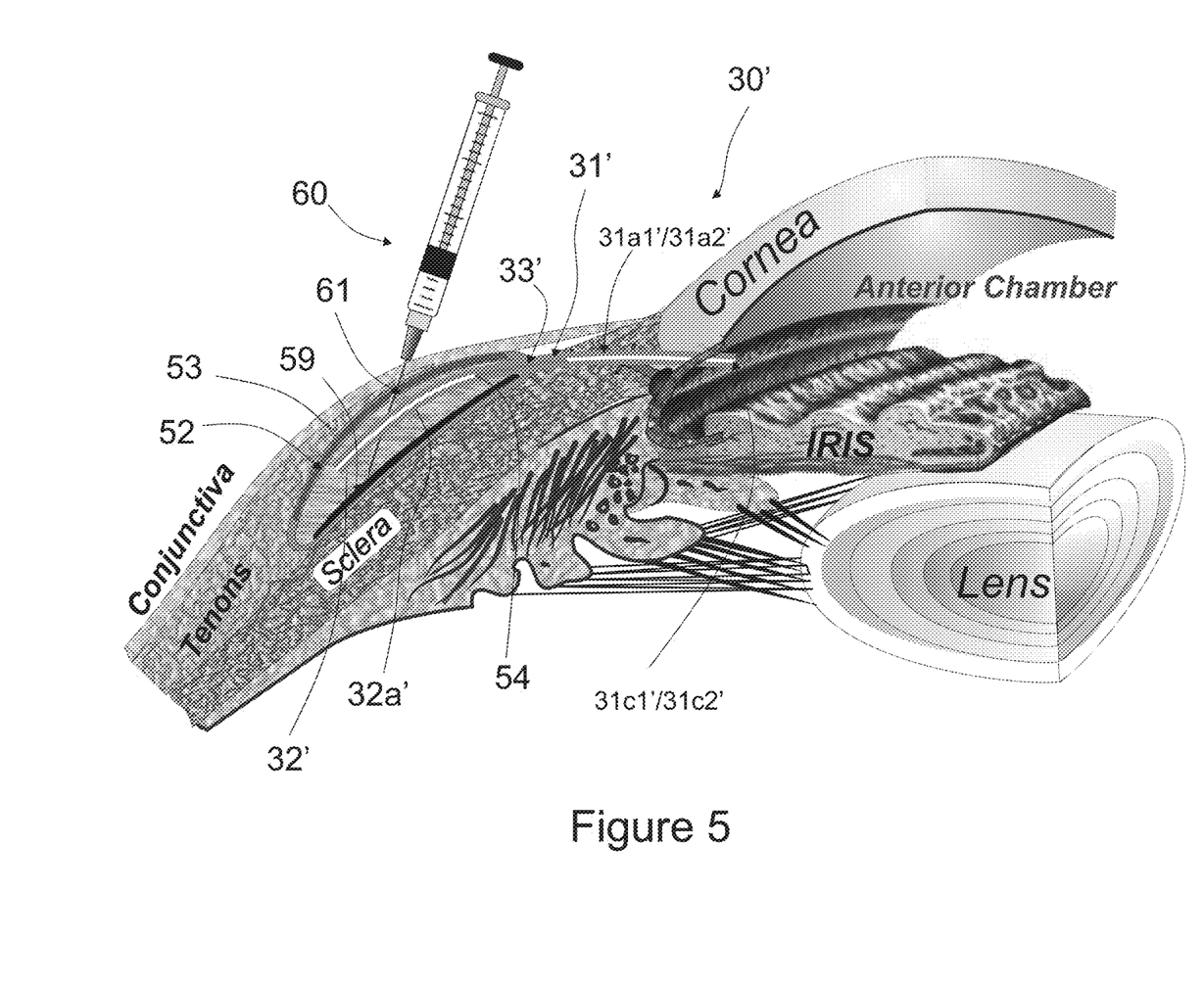
FIG. 5 is a diagram that shows an example implantation or placement of a drug delivery device or system (DDS) that includes the ocular implant of FIGS. 3A and 3B.
Figure 6:
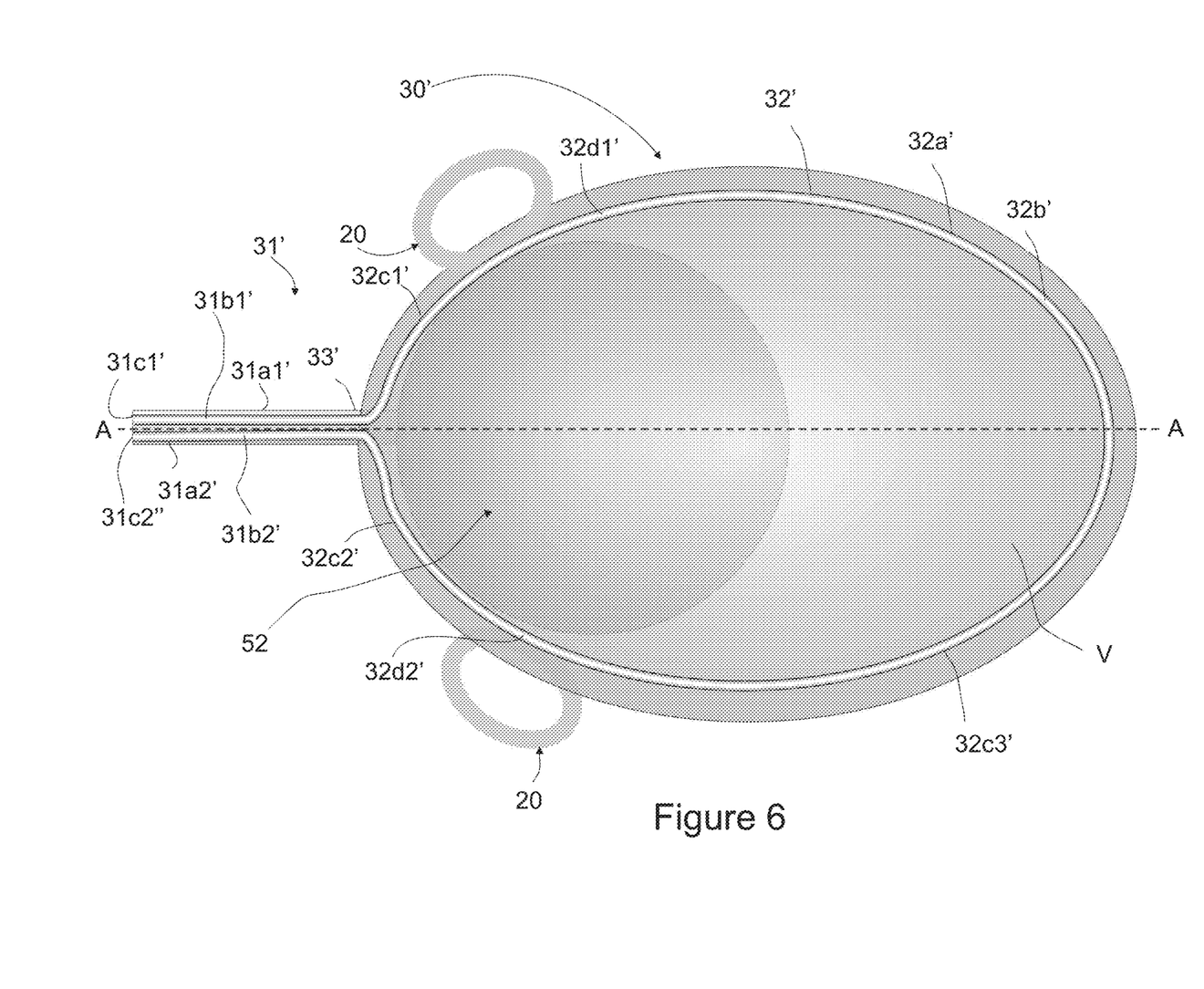
FIG. 6 is a top plan view schematic diagram of the DDS of FIG. 5 implanted into the eye.

A drug delivery device or system (DDS) 51 for treating ocular diseases is shown in FIGS. 5 and 6 that employs a self-sealing reservoir 52 that can be loaded to hold a volume of a liquid-form therapeutic agent. In FIGS. 5 and 6, the DDS 51 is shown including an implant 30' corresponding to the ocular implant 30 discussed above. In FIGS. 5 and 6, corresponding features of ocular implant 30 are shown appended with a "'". The ocular implant 30' has the same structure as ocular implant 30 of FIGS. 3A and 3B unless specified otherwise herein.

DDS 51 includes a fluid reservoir 52 formed by a self-sealing polymeric membrane 53 and a base 54. The base 54 can have a bottom concave surface that is contoured to interface and rest naturally in an implanted configuration on ocular tissue that forms the globe of the human eye.

The ocular implant 30' is fluidly coupled to the fluid reservoir 52. Specifically, the second loop portion 32' is contained within the reservoir 52 and the first duct portion 31' extends from the second loop portion 32' and through the membrane 53 of the reservoir 52. The outer surfaces of the tubes 31$a$1', 31$a$2' of the first duct portion 31' sealably extend through a wall of the reservoir 52. The at least one opening (e.g., openings 32$d$1', 32$d$2') of the looped tube 32$a$' is in fluid communication with the fluid (e.g., liquid form agent) in the reservoir 52 and permits the fluid held by the reservoir to enter through the at least one opening (e.g., openings 32$d$1', 32$d$2') for delivery through the lumen of the second loop portion, and through the lumens 32$b$1', 32$b$2' of the duct portion 31', where the fluid exits through the open ends or outlets 31$c$1', 31$c$2' of the duct portion 31' and into the eye.

The DDS 51 can be implanted in the eye so that some or all parts of the DDS 51 are surrounded and covered by ocular tissue and where the open ends or outlets 31$c$1', 31$c$2' of the duct portion 31' are located in a desired drug delivery location, such as the anterior chamber of the eye.

As shown in FIG. 5, the self-sealing polymeric membrane 53 is configured to be pierced by a needle 60 in order to fill and/or refill the internal space of the reservoir 52 with the desired liquid-form therapeutic agent. When a needle 60 is inserted through the self-sealing membrane 53 and removed, the polymeric material of the membrane 53 effectively seals the needle tract thereby preventing fluid held in the fluid reservoir 52 from escaping out through the needle tract.

Note that SIBS is preferably used for the DDS 51 and the ocular implant 30' as it is biocompatible, soft, atraumatic, bioinert and has proven history in the eye greater than 10-years in duration. The base 54 can be formed from one or more polymer layers with a thin hard needle stopper feature 59. The needle stopper feature 59 can be placed on or bonded to the inside surface of the base 54 or possibly formed as part of the base 54. The polymer layer(s) of the base 54 can be realized from SIBS, silicon rubber or other suitable polymeric material. The needle stopper feature 59 can be realized from a metal (such as titanium or stainless steel) or a hard plastic (such as polyimide, polyacetal or polysulfone). In one embodiment, the needle stopper feature 59 is formed from titanium of 0.002" thickness. Titanium is used here due to its well-established history in the body and its lack of interference with MRI. When using the needle to fill or refill the reservoir, the needle stopper feature 59 prevents the needle that pierces the sealing membrane 53 from entering into and passing through the base 54 and possibly injuring the eye that underlies the base 54 as well as providing a pin-hole where liquid-form therapeutic agent can escape.

Furthermore, the polymeric materials of the self-sealing membrane 53, the base 54 and the tubes 31$a$' and 32$a$' can be selected to be impervious to the therapeutic agent held within the reservoir 52 and thus prevent diffusion of the therapeutic agent through the walls of the reservoir 52 or through the annular wall along the lengthwise extent of the tubes 31$a$' and 32$a$'.

The DDS 51 can also include fixations structures or ears 20 that can aid in fixating the DDS 51 at a desired implantation location in the eye (for example, by suturing through the ears 20 into ocular tissue such as the sclera). In embodiments, the reservoir 52 of the DDS 51 can be implanted at location under the conjunctiva and Tenon's Capsule in the eye such that the contoured base 54 sits on the sclera of the eye. The radius of curvature of the contour of the base 54 is approximately 0.5 inches (12.5 mm). Further details of the DDS 51 are set forth in PCT Patent Appl. No. PCT/US21/17412, filed on Feb. 10, 2021, herein incorporated by reference in its entirety.

In yet other embodiments, the DDS of FIGS. 5 and 6 can be configured to employ any one of the tubular implants described below with respect to FIGS. 7A to 7C to deliver fluid (e.g., liquid form therapeutic agent) from the fluid reservoir of the DDS through the lumens of the ocular implant and to the target site of the eye, such as to the anterior chamber of the eye.

Figure 7A:
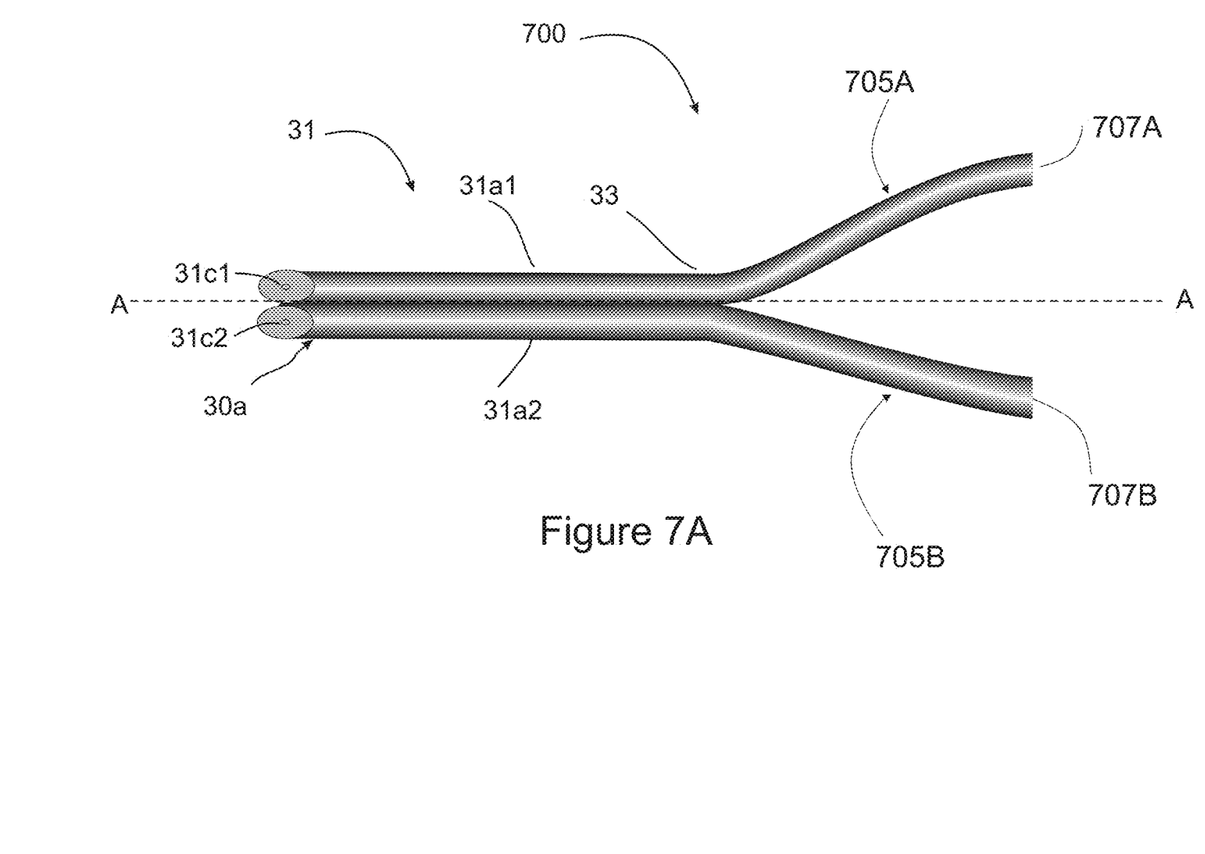
FIG. 7A shows yet another example embodiment of an ocular implant in accordance with the present disclosure.

FIG. 7A illustrates an embodiment of an ocular implant 700 similar to the ocular implant of FIGS. 3A and 3B where the looped tube (racquet head) is replaced by two separate tube segments or legs 705A and 705B that extend or flare outwardly from the neck 33 opposite one another relative to the longitudinal axis A-A in a Y configuration as shown. The two tube segments 705A and 705B have corresponding fluid exits or outlets 707A and 707B. Tube segment 705A has an internal lumen that is in fluid communication with the internal lumen of tube 31$a$l of the duct section 31 at the neck 33. This lumen extends from the neck 33 to the fluid exit 707A. Similarly, tube segment 705B has an internal lumen that is in fluid communication with the internal lumen of tube 31$a$2 of the duct section 31 at the neck 33. This lumen extends from the neck 33 to the fluid exit 707B. The ocular implant 700 can be implanted in the eye to permit aqueous humor in the anterior chamber of the eye to flow into the inlets 31$c$1, 31$c$2 of the tubes 31$a$1, 31$a$2 of the duct portion 31, through the two internal lumens of the two tubes 31$a$1, 31$a$2, through the internal lumens of the separate tube segments 705A, 705B, and then out the corresponding fluid exits 707A, 707B and into a bleb, where the fluid can be further transported (e.g., absorbed) through the tissues surrounding the bleb. When the ocular implant 700 is implanted as described above, the ocular implant 700 can be titratable by temporarily blocking or plugging the internal lumen of either tube segment 705A or 705B. The plugging can be accomplished by a suture, a wire or a ligating suture or band, or other suitable structure. The plug can be removed after implant to provide more flow and lower intraocular pressure, if desired.

Figure 7B:
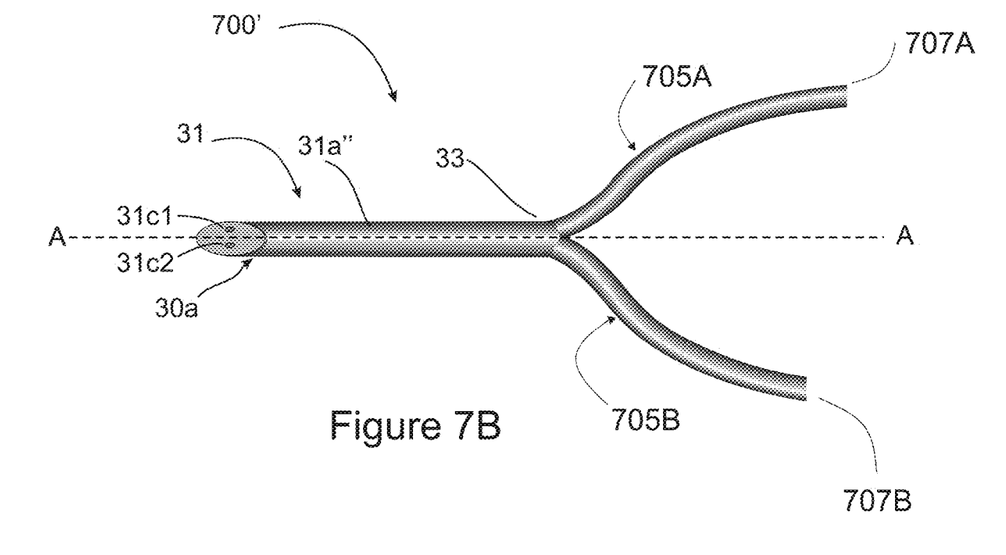
FIG. 7B shows still another example embodiment of an ocular implant in accordance with the present disclosure.

FIG. 7B illustrates an embodiment of an ocular implant 700' similar to the ocular implant of FIG. 7A where the looped tube (racquet head) is replaced by two separate tube segments or legs 705A and 705B that extend or flare outwardly from the neck 33 opposite one another relative to the longitudinal axis A-A in a Y configuration as shown. The two tube segments 705A and 705B have corresponding fluid exits or outlets 707A and 707B. In this embodiment, the duct portion 31 includes a single tube 31a" that defines two separate internal lumens that are in fluid communication with the internal lumens of the two tube segments 705A, 705B at the neck 33. A single tube may be easier to pass under the limbus to enter the anterior chamber. Tube segment 705A has an internal lumen that is in fluid communication with one of the internal lumens of tube 31a" at the neck 33. This lumen extends from the neck 33 to the fluid exit 707A. Similarly, tube segment 705B has an internal lumen that is in fluid communication with the other one of the internal lumens of tube 31a" at the neck 33. This lumen extends from the neck 33 to the fluid exit 707B. The ocular implant device 700' can be implanted in the eye to permit aqueous humor in the anterior chamber of the eye to flow into the inlets 31c1, 21c2 of the tube 31a", through the two internal lumens of the tube 31a", through the internal lumens of the separate tube segments 705A, 705B, and then out the corresponding fluid exits 707A, 707B and into a bleb, where the fluid can be further transported (e.g., absorbed) through the tissues surrounding the bleb. When the ocular implant device 700' is implanted as described above, the ocular implant device 700' can be titratable by temporarily blocking or plugging the internal lumen of either tube segment 705A or 705B. The plugging can be accomplished by a suture, a wire or a ligating suture or band, or other suitable structure. The plug can be removed after implant to provide more flow and lower intraocular pressure, if desired.

Figure 7C:
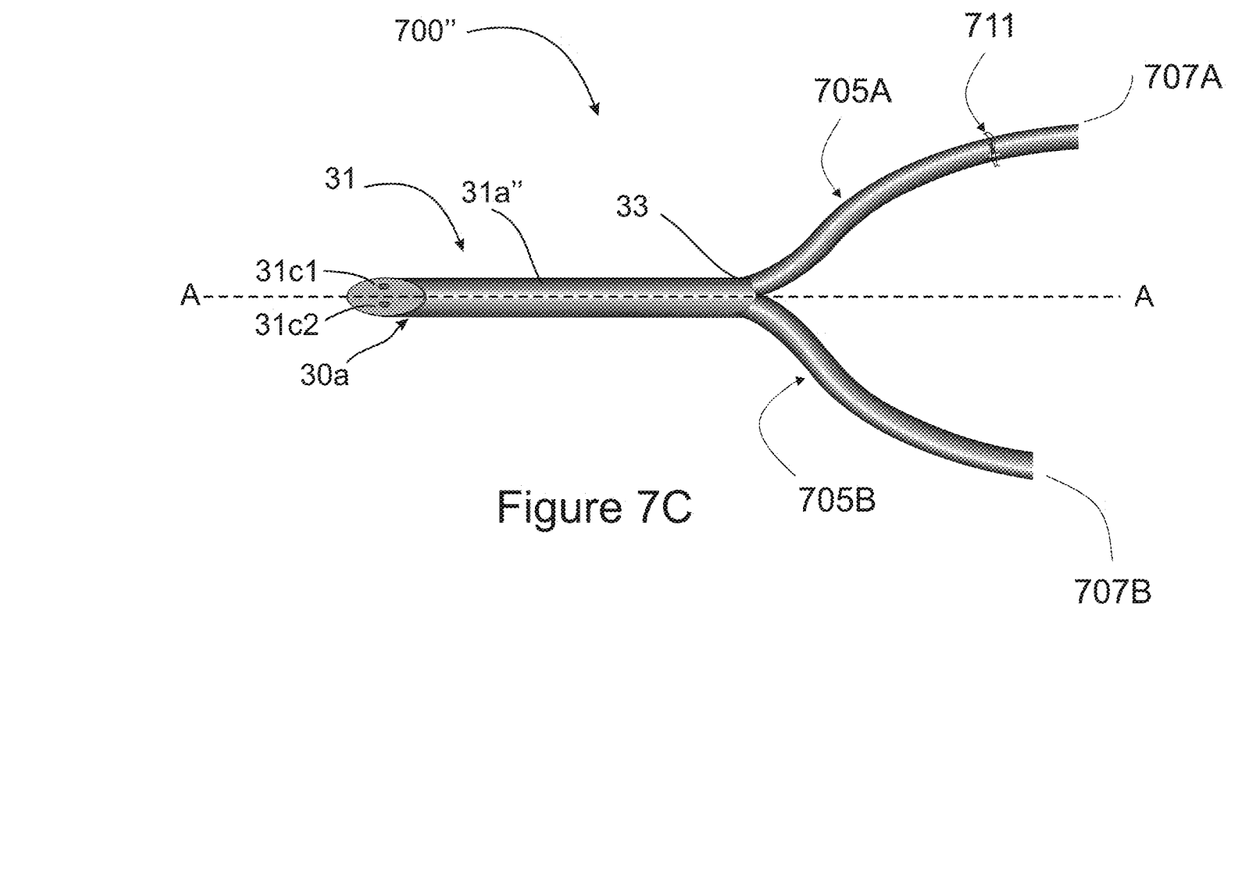
FIG. 7C shows another example embodiment of an ocular implant in accordance with the present disclosure.

FIG. 7C illustrates an embodiment of an ocular implant 700" similar to the ocular implant of FIG. 7B where the tube segment 705A has a loop or ligature 711 compressing the tube segment 705A to selectively or temporarily occlude flow through the internal lumen of tube segment 705A. In the event that more flow is required, the loop or ligature 711 can be laser lysed or simply cut with a scissors or knife. In alternate embodiments, ligature 711 can be substituted by a factory-installed compression band that can be laser relaxed to open the internal lumen of tube segment 705A.

In embodiments, one or more of the ocular implants of FIGS. 7A, 7B and 7C can be formed from a flexible elastomeric material. For example, such ocular implant(s) can be formed from SIBS as described herein. In embodiments, the hardness of the elastomeric polymer material of such ocular implant can range from Shore 30 A to Shore 65D, preferably shore 40 A to 50 A. In the event that the duct portion 31 and branched tubular segments 705A and 705B are formed from different polymeric materials (such as different SIBS materials), the duct portion 31 can be formed from an elastomeric polymer material (e.g., first SIBS material) with a hardness in the range of Shore 40 A to Shore 50 A, while the branched tubular segments 705A and 705B can be from a different elastomeric polymer material (e.g., second SIBS material) with a hardness in the range of Shore 80 A to Shore 65D and more preferably in the range of Shore 50D to Shore 55D. These material properties can provide some rigidity to the branched tubular segments 705A and 705B to ensure that the branched tubular segments do not fold on themselves in the bleb.

In embodiments, when one or more of the ocular implants of FIGS. 7A, 7B and 7C are implanted in the eye, the duct portion 31 of such ocular implant(s) can extend in a straight linear path, curved linear path, segmented path or other complex curvilinear path depending on the design and material properties (e.g., hardness) of the duct portion 31. For flexible configurations of the duct portion 31, the path of the duct portion 31 can depend on placement of the duct portion 31 and the surrounding ocular tissue in the eye. Similarly, when one or more of the ocular implants of FIGS. 7A, 7B and 7C are implanted in the eye, the branched tube segments 705A, 705B of such ocular implant(s) can extend in a straight linear path, a curved linear path, segmented path or other complex curvilinear path depending on the design and material properties (e.g., hardness) of the respective tube segments 705A, 705B. For flexible configurations of the tube segments 705A, 705B, the path of the tube segments 705A, 705B can depend on placement of the tube segments 705A, 705B and the surrounding ocular tissue in the eye.

There have been described and illustrated herein several embodiments of an ocular implant device and related drug delivery systems, methods of treatment, and methods of manufacture. While particular embodiments of the invention have been described, it is not intended that the invention be limited thereto, as it is intended that the invention be as broad in scope as the art will allow and that the specification be read likewise. Thus, while particular tubular constructions of the ocular implants have been disclosed, it will be appreciated that other constructions may be used as well as well. For example, while an ocular implant formed from a single tube is preferred, it will be recognized that other constructions are possible. In addition, while particular types of materials used for the ocular implant have been disclosed, it will be understood that other similar suitable materials can be used. It will therefore be appreciated by those skilled in the art that yet other modifications could be made to the provided invention without deviating from its spirit and scope as claimed.

What is claimed is:

1. A device implantable into the eye, comprising:
an elongate duct portion having a longitudinal axis, the duct portion defining two lumens that extend parallel to one another from a distal end to a neck spaced longitudinally from the distal end; and
a second portion including tubular segments that extend or flare outwardly from the neck opposite one another relative to the longitudinal axis and form a tubular loop that surrounds an interior area, wherein the tubular segments of the second portion that form the tubular loop define an enclosed lumen with a plurality of separate and distinct outlets or openings spaced apart from one another that are in fluid communication with the two lumens of the duct portion to permit fluid to flow through the device;
wherein the elongate duct portion and the tubular loop are formed together as a unitary structure that forms a closed loop prior to implantation of the device.

2. A device according to claim 1, wherein:
the tubular segments of the second portion define parts of the enclosed lumen; and
the two parallel lumens of the duct portion are in fluid communication with the enclosed lumen.

3. A device according to claim 1, wherein:
the duct portion and the second portion are made of SIBS (poly(styrene-block-isobutylene-block-styrene)).

4. A device according to claim 1, wherein:
the plurality of separate and distinct outlets or openings lead from the enclosed lumen to a bleb formed by ocular tissue.

5. A device according to claim 4, wherein:
the tubular segments of the second portion that form the tubular loop have surfaces that contact and interface to tissue surfaces that define the bleb.

6. A device according to claim 1, further comprising:
a loop or band that surrounds one tubular segment of the two tubular segments of the second portion and that is configured to selectively occlude flow through the internal lumen of the one tubular segment.

7. A drug delivery device comprising:
the device according to claim 1; and
a fluid reservoir configured to hold a supply of liquid-form therapeutic agent, wherein the second portion of the device of claim 1 is disposed within the fluid reservoir, and wherein the duct portion of the device of claim 1 extends outside the reservoir, wherein the device of claim 1 is configured to permit the liquid-form therapeutic agent to flow through the device.

8. A drug delivery device according to claim 7, wherein:
at least a portion of the fluid reservoir is self-sealing and is configured to be punctured by a syringe needle for filling the fluid reservoir with the liquid-form therapeutic agent.

9. A method for treating an eye, comprising:
providing a device according to claim 1;
disposing the distal end of the duct portion of the device in the anterior chamber of the eye; and
positioning the second portion of the device in a drainage cavity or bleb defined by ocular tissue;
wherein at least one lumen of the duct portion and at least one outlet or opening of the second portion of the device permit aqueous humor in the anterior chamber to flow through the device into the drainage cavity or bleb.

10. A method according to claim 9, wherein:
the drainage cavity or bleb is disposed between Tenon's capsule and the sclera of the eye.

11. A method according to claim 9, wherein:
surfaces of the second portion of the device contact and interface to the ocular tissue that defines the drainage cavity or bleb.

12. A method according to claim 9, wherein:
the plurality of separate and distinct outlets or openings in the tubular segments of the second portion lead from the enclosed lumen to the drainage cavity or bleb.

* * * * *